(12) United States Patent
Old

(10) Patent No.: US 7,781,465 B2
(45) Date of Patent: *Aug. 24, 2010

(54) THERAPEUTIC OXAZOLIDINONES AND THIAZOLIDINONES

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/192,230

(22) Filed: Aug. 15, 2008

(65) Prior Publication Data

US 2009/0054505 A1    Feb. 26, 2009

Related U.S. Application Data

(60) Provisional application No. 60/957,075, filed on Aug. 21, 2007.

(51) Int. Cl.
A61K 31/427 (2006.01)
A61K 31/422 (2006.01)
C07D 277/04 (2006.01)
C07D 263/04 (2006.01)

(52) U.S. Cl. ............... 514/369; 514/376; 548/182; 548/225

(58) Field of Classification Search ............ 514/369, 514/376; 548/182, 225
See application file for complete search history.

(56) References Cited

U.S. PATENT DOCUMENTS

| | | | |
|---|---|---|---|
| 4,225,609 | A | 9/1980 | Cragoe |
| 7,183,324 | B2 | 2/2007 | Donde |
| 7,476,747 | B2 | 1/2009 | Old |
| 2005/0209336 | A1 | 9/2005 | Borman |
| 2007/0129552 | A1 | 6/2007 | Donde |

OTHER PUBLICATIONS

Shih, C.; et al. "Synthesis and Biological Activity of Acyclic Analogues of 5,10-Dideaza-5,6,7,8-tetrahydrofolic Acid" J. Med. Chem. 1992, 35, 1109-1116.
Silverman, Richard B., "Prodrugs and Drug Delivery Systems". Organic Chemistry of Drug Design and Drug Action, 2d Ed., Elsevier Academic Press: Amsterdamn, 2004, pp. 496-557.
U.S. Appl. No. 60/894,369, filed Mar. 12, 2007, Garst.

Primary Examiner—Kamal A Saeed
Assistant Examiner—Samantha L Shterengarts
(74) Attorney, Agent, or Firm—Kevin J. Forrestal; John E. Wurst

(57) ABSTRACT

Disclosed herein is a compound represented by a formula

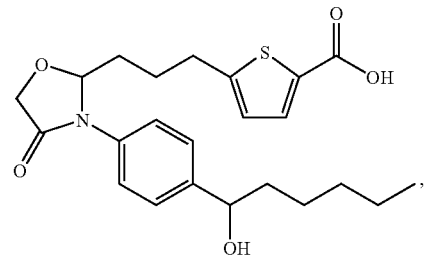

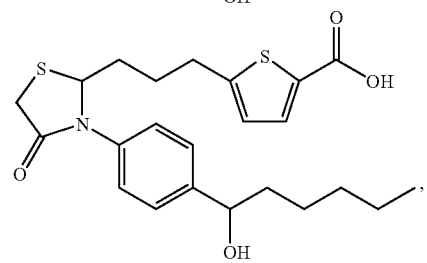

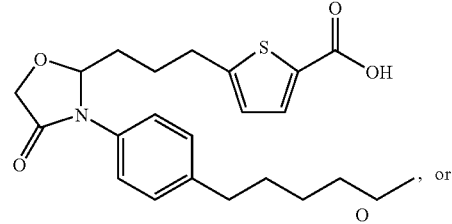

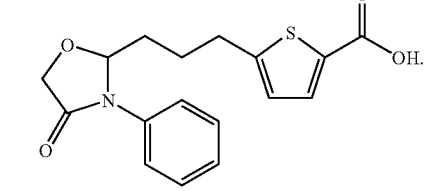

Therapeutic methods, compositions, and medicaments related thereto are also disclosed.

19 Claims, No Drawings

THERAPEUTIC OXAZOLIDINONES AND THIAZOLIDINONES

CROSS REFERENCE TO RELATED APPLICATIONS

This application claims priority to U.S. Provisional Patent Application No. 60/957,075, filed Aug. 21, 2007, which is incorporated by reference herein.

DESCRIPTION OF THE INVENTION

Disclosed herein is a compound represented by a formula

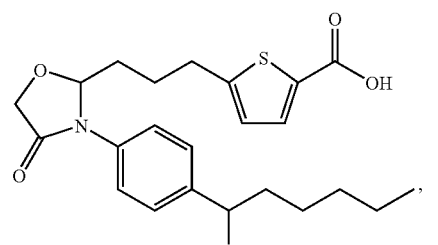,

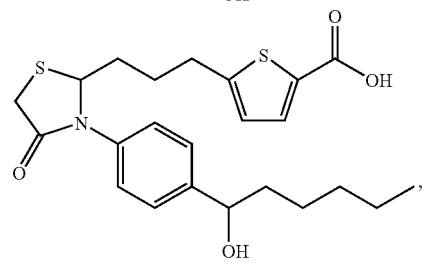,

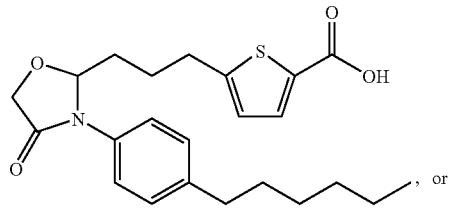, or

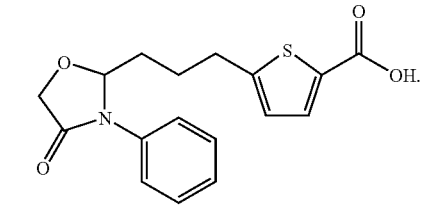.

The compounds below are specifically contemplated.

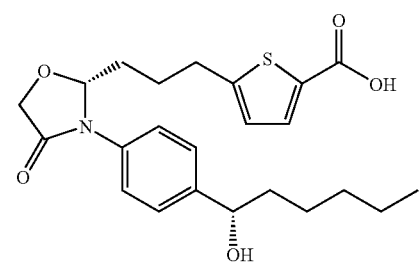

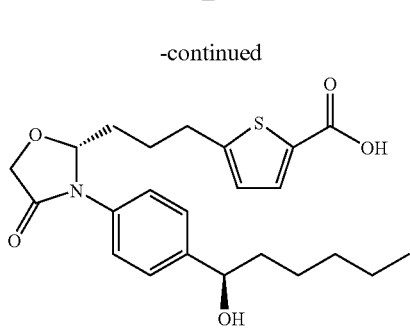

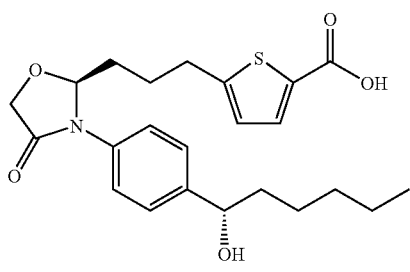

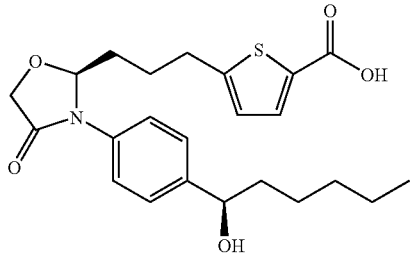

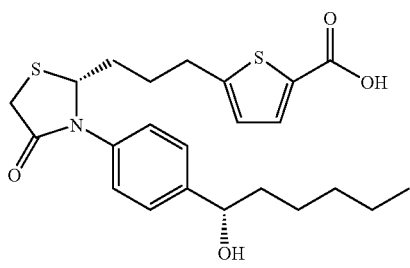

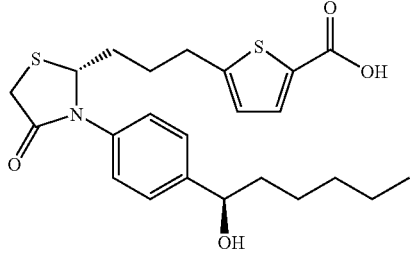

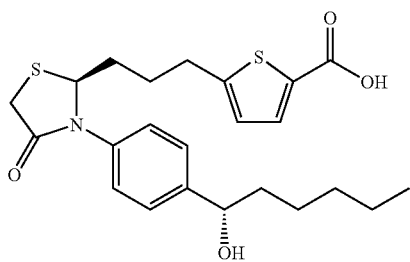

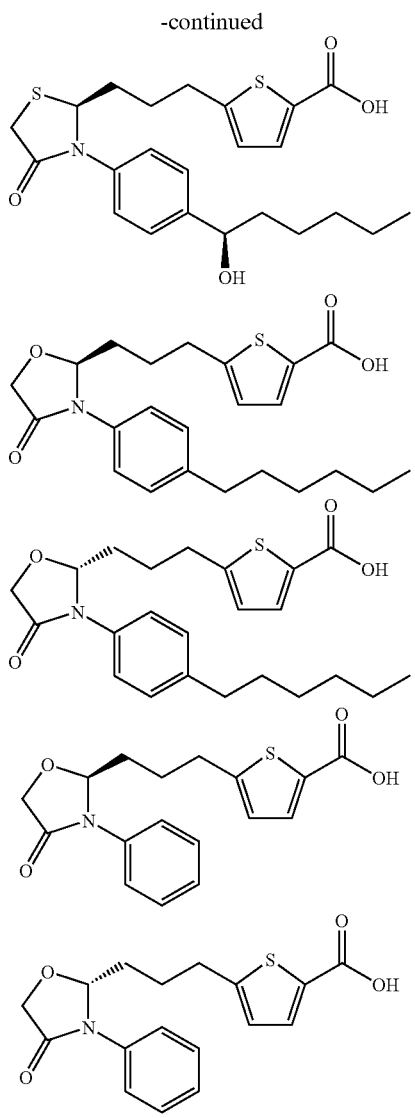

These compounds are useful for the treatment of glaucoma and the reduction of intraocular pressure. The compound is incorporated into a dosage form or a medicament and administered to the mammal, such as a person, in need thereof. For example, a liquid composition may be administered as an eye drop or a solid or liquid dosage form may also be administered orally. Other types of dosage forms and medicaments are well known in the art, and may also be used here.

Another embodiment is a composition comprising a compound disclosed herein, wherein said composition is a liquid which is ophthalmically acceptable.

Another embodiment is a medicament comprising a compound disclosed herein, wherein said medicament is a liquid which is ophthalmically acceptable.

Another embodiment is a method comprising administering a compound disclosed herein to a mammal for the reduction of intraocular pressure.

Another embodiment is use of a compound disclosed herein in the manufacture of a medicament for the treatment of glaucoma or ocular hypertension.

Another embodiment is a kit comprising a composition comprising compound disclosed herein, a container, and instructions for administration of said composition to a mammal for the treatment of glaucoma or elevated intraocular pressure.

Methods of formulating compounds such as those disclosed herein for ophthalmic and other pharmaceutical preparations are well known in the art. For example, U.S. patent application Ser. No. 10/599,046, filed on Sep. 18, 2006, incorporated by reference herein, describes typical formulation methods.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group, such as a $C_{1-6}$ alkyl ester of the carboxylic acid group of the present compounds, or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

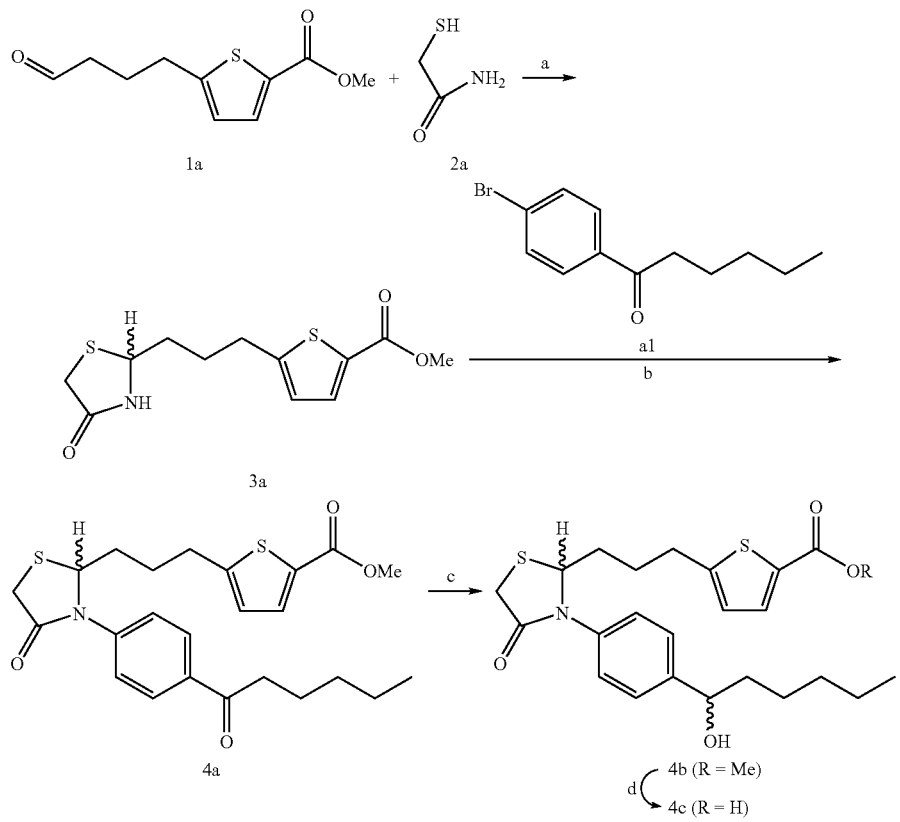

(a) p-TsOH, toluene, reflux; (b) a1, Pd₂(dba)₃, Xantphos, Cs₂CO₃, dioxane, reflux; (c) NaBH₄, MeOH, CH₂Cl₂; (d) LiOH (aq.), THF.

EXAMPLE 1

5-(3-(3-(4-(1-hydroxyhexyl)phenyl)-4-oxo-thiazolidin-2-yl)propyl)thiophene-2-carboxylic acid (4c)

Step 1. Condensation of 1a and 2a to give 3a

A mixture of methyl 5-(4-oxobutyl)thiophene-2-carboxylate (1a, see Cragoe, et al. U.S. Pat. No. 4,225,609; also prepared by Swern oxidation of the corresponding alcohol prepared as described by Shih, C., et. al. J. Med. Chem. 1992, 35, 1109-1116; 5.3 g, 25.0 mmol) and 2-mercaptoacetamide (2a, 6.76 g, 74.2 mmol) in toluene (50 mL) was refluxed in a flask fitted with a Dean-Stark trap. p-Toluenesulfonic acid monohydrate (3.8 g, 20.0 mmol) was added portionwise over several hours. After a total of 5 hours at reflux, the mixture was cooled and the toluene layer was decanted. Additional toluene (50 mL) was used to wash the oily remainder and then was decanted. The combined organic phase was washed with water (2×100 mL), saturated aqueous NaHCO₃ (100 mL), water (100 mL) and brine (100 mL) then filtered through filter paper and concentrated in vacuo to afford 1.7 g of crude product. Purification of the residue on silica (hexane→EtOAc, gradient) afforded 1.08 g of thiazolidinone 3a. This product was recrystallized from hot MeOH (3 mL) to afford 800 mg of 3a (11%).

Step 2. Arylation of 3a with a1 to give 4a

Pd₂(dba)₃ (41 mg, 0.045 mmol), Xantphos (77 mg, 0.133 mmol) and Cs₂CO₃ (428 mg, 1.31 mmol) were added sequentially to a solution of 3a (314 mg, 1.10 mmol) and a1 (see Borman, et al., United States Patent Application Publication No. 2005/0209336, incorporated by reference herein; 255 mg, 1.00 mmol) in 1,4-dioxane (7.1 mL). The flask was fitted with a reflux condenser, evacuated and refilled with nitrogen (5×) then heated at reflux. After 3 d, the reaction was cooled, diluted with EtOAc (50 mL) and filtered through celite, washing with excess EtOAc. The EtOAc filtrate was concentrated in vacuo. The crude residue was purified on 40 g silica gel (hexanes→EtOAc, gradient) to afford 56 mg (12%) of 4a.

Step 3. Reduction of 4a to give 4b

Sodium borohydride (7 mg, 0.19 mmol) was added to a solution of 4a (55 mg, 0.12 mmol) in MeOH (0.30 mL) and CH₂Cl₂ (0.30 mL). After 18 h at room temperature the reaction was quenched with 1 N HCl (5 mL) and extracted with EtOAc (3×20 mL). The combined organic phase was dried (Na₂SO₄), filtered and concentrated in vacuo. The crude residue was purified on 12 g silica gel (hexanes→EtOAc, gradient) to afford 9 mg (16%) of 4b.

Step 4. Saponification of 4b to give 4c

Lithium hydroxide (0.10 mL of a 1.0 N solution in water, 0.10 mmol) was added to a solution of 4b (9 mg, 0.019 mmol) in THF (0.19 mL). The reaction mixture was heated at 40° C. After 24 h at 40° C., the reaction mixture was cooled to room temperature and the mixture was concentrated under a stream of nitrogen. The residue was diluted with water (0.2 mL), acidified with 1 N HCl (0.5 mL) and extracted with EtOAc (3×2 mL). The combined organic phase was washed with brine (2 mL), dried (Na₂SO₄), filtered and concentrated in vacuo. Purification of the crude residue by chromatography on 4 g silica gel (CH₂Cl₂→20% MeOH/CH₂Cl₂, gradient) afforded 5 mg (57%) of 4c.

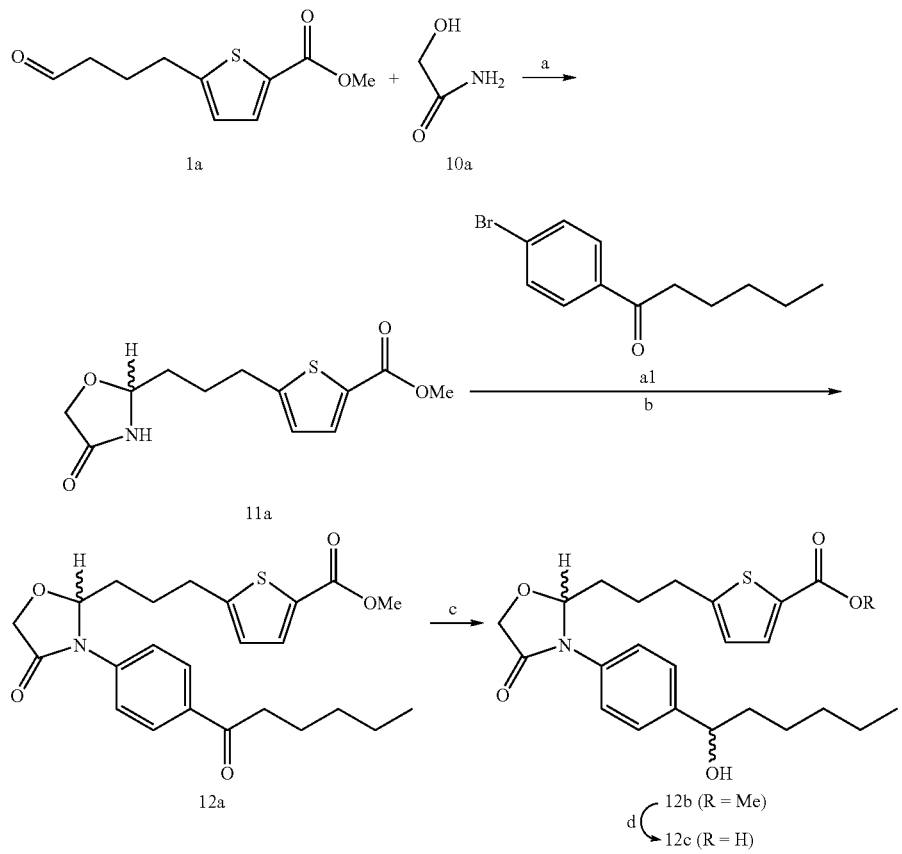

(a) p-TsOH, toluene, reflux; (b) a1, Pd₂(dba)₃, Xantphos, Cs₂CO₃, dioxane, reflux; (c) NaBH₄, MeOH, CH₂Cl₂; (d) LiOH (aq.), THF.

EXAMPLE 2

5-(3-(3-(4-(1-hydroxyhexyl)phenyl)-4-oxo-oxazolidin-2-yl)propyl)thiophene-2-carboxylic acid (12c)

Step 1. Condensation of 1a and 10a to give 11a

A mixture of 1a (2.75 g, 13.0 mmol), 2-hydroxyacetamide (10a, 2.9 g, 38.6 mmol) and p-toluenesulfonic acid monohydrate (250 mg, 1.3 mmol) in toluene (20 mL) was refluxed in a flask fitted with a Dean-Stark trap. After 2 h, the reaction was cooled and partitioned between water (20 mL) and EtOAc (20 mL). The organic phase was separated and washed with water (2×50 mL) and 1 M NH₄OH (50 mL), filtered through filter paper and concentrated in vacuo. Purification of the residue on silica (hexane→EtOAc, gradient) afforded 300 mg of oxazolidinone 11a (9%).

Step 2. Arylation of 11a with a1 to give 12a

Pd₂(dba)₃ (41 mg, 0.045 mmol), Xantphos (77 mg, 0.133 mmol) and Cs₂CO₃ (428 mg, 1.31 mmol) were added sequentially to a solution of 11a (297 mg, 1.10 mmol) and a1 (256 mg, 1.00 mmol) in 1,4-dioxane (7.1 mL). The flask was fitted with a reflux condenser, evacuated and refilled with nitrogen (5×) then heated at reflux. After 18 h, the reaction was cooled, diluted with EtOAc (50 mL) and filtered through celite, washing with excess EtOAc. The EtOAc filtrate was concentrated in vacuo. The crude residue was purified on 40 g silica gel (hexanes→50% EtOAc/hexanes, gradient) to afford 363 mg (82%) of 12a as a pale yellow solid.

Step 3. Reduction of 12a to give 12b

Sodium borohydride (22 mg, 0.58 mmol) was added to a solution of 12a (130 mg, 0.29 mmol) in MeOH (0.75 mL) and CH₂Cl₂ (0.75 mL). After 1 h at room temperature the reaction was quenched with 1 N HCl (5 mL) and extracted with EtOAc (3×25 mL). The combined organic phase was dried (Na₂SO₄), filtered and concentrated in vacuo. The crude residue was purified on 12 g silica gel (hexanes→EtOAc, gradient) to afford 130 mg (99%) of 12b.

Step 4. Saponification of 12b to give 12c

Lithium hydroxide (0.72 mL of a 1.0 N solution in water, 0.72 mmol) was added to a solution of 12b (64 mg, 0.14 mmol) in THF (0.72 mL). The reaction mixture was heated at 40° C. After 8 h at 40° C., the reaction mixture was cooled to room temperature and the mixture was concentrated under a stream of nitrogen. The residue was diluted with water (2 mL), acidified with 1 N HCl (2 mL) and extracted with EtOAc (3×10 mL). The combined organic phase was dried (Na₂SO₄), filtered and concentrated in vacuo. Purification of the crude residue by chromatography on 4 g silica gel (40% EtOAc/hexanes→EtOAc, gradient) afforded 5 mg (8%) of 12c.

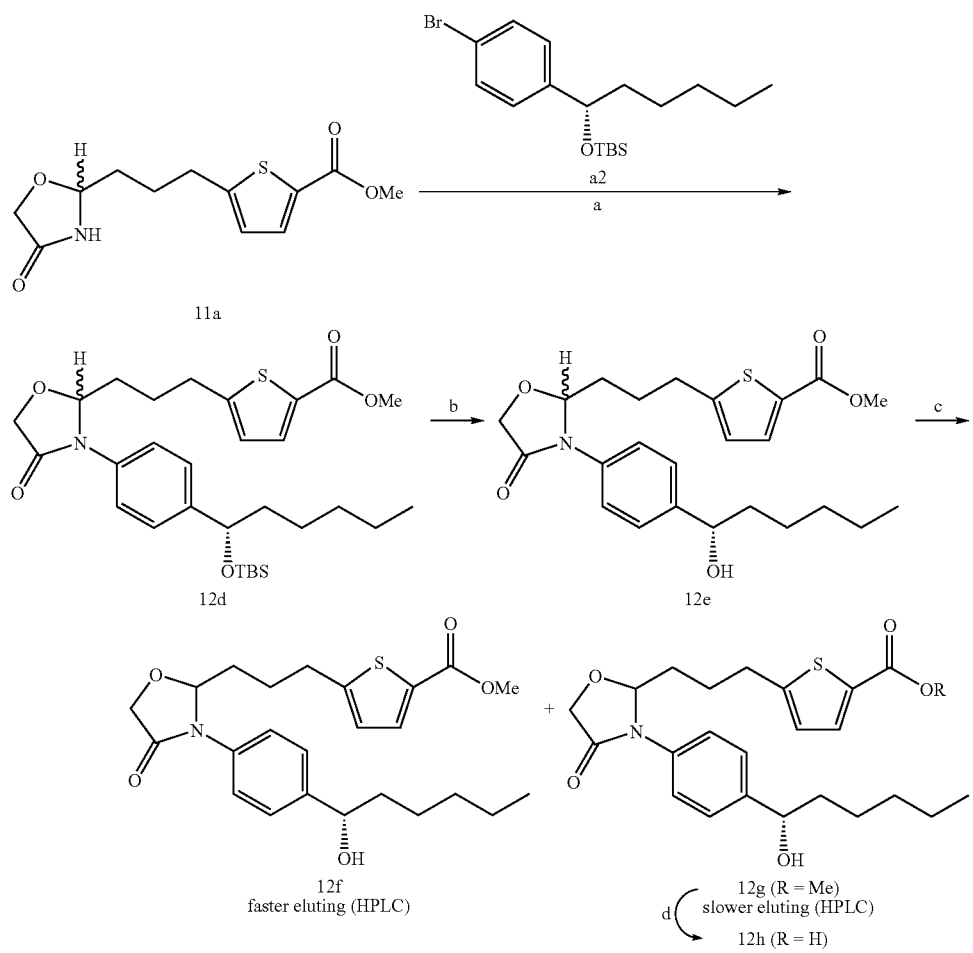

(a) CuI, MeN(H)CH₂CH₂N(H)Me, K₂CO₃, MeCN, reflux; (b) HF-pyridine, MeCN; (c) HPLC separation; (d) Rabbit liver esterase, pH 7.2 buffer, MeCN.

EXAMPLE 3

5-(3-(3-(4-((S)-1-hydroxyhexyl)phenyl)-4-oxooxazolidin-2-yl)propyl)thiophene-2-carboxylic acid (12h)

Step 1. Arylation of 1a with a2 to give 12d

Potassium carbonate (276 mg, 2.0 mmol), copper(I) iodide (19 mg, 0.10 mmol) and N,N'-dimethylethylene diamine (21.5 µL, 0.2 mmol) were added sequentially to a solution of 11a (296 mg, 1.10 mmol) and a2 (see U.S. Provisional Patent Application No. 60/894,369, filed Mar. 12, 2007, incorporated by reference herein, 371 mg, 1.0 mmol) in MeCN (2.5 mL). The reaction flask was fitted with a reflux condenser, the mixture was degassed with nitrogen by evac/fill (5×) and then heated at reflux. After 4 d, the mixture was cooled, diluted with EtOAc and filtered through celite, washing with excess EtOAc. The filtrate was concentrated in vacuo. The crude residue was purified on 40 g silica (hexanes→EtOAc, gradient) to afford 33 mg (6%) of 12d.

Step 2. Deprotection of 12d to give 12e

HF-pyridine (100 µL) was added to a solution of 12d (33 mg, 0.059 mmol) in MeCN (1.2 mL) at 0° C. in a plastic scintillation vial. After 45 min at 0° C., the reaction was allowed to warm to room temperature. After 1 h at room temperature, the reaction was quenched with saturated aqueous NaHCO₃ (5 mL) and extracted with EtOAc (3×15 mL). The combined organic phase was dried (Na₂SO₄), filtered and concentrated in vacuo. The crude residue was purified on 4 g silica (hexanes→EtOAc, gradient) to afford 14 mg (53%) of 12e.

Step 3. HPLC separation of 12e to give 12f and 12g

The two diastereomers of 12e (14 mg) were separated on a Waters 600 HPLC instrument employing a Waters 2996 PDA detector and a Phenomenex Luna 10µ prep silica (2) 1 column, 50 mm×250 mm (p/no. 00G-4322-V0; s/no. 356757-1). Using a flow rate of 45 mL/min and 50% EtOAc/Hex as the eluent, the first diastereomer (12f, 6 mg) eluted at 87-96 min, and the second diastereomer (12g, 6 mg) eluted at 97-106 min.

Step 4. Saponification of 12g to give 12h

Rabbit liver esterase (5 mg) was added to a mixture of 12g (6 mg, 0.013 mmol), MeCN (0.1 mL) and pH 7.2 buffer (2.0 mL). The reaction mixture was stirred vigorously for 6 days at room temperature then was concentrated in vacuo. The residue was suspended in CH₂Cl₂ and filtered through celite. The filtrate was concentrated in vacuo to afford 2.5 mg (43%) of 12h.

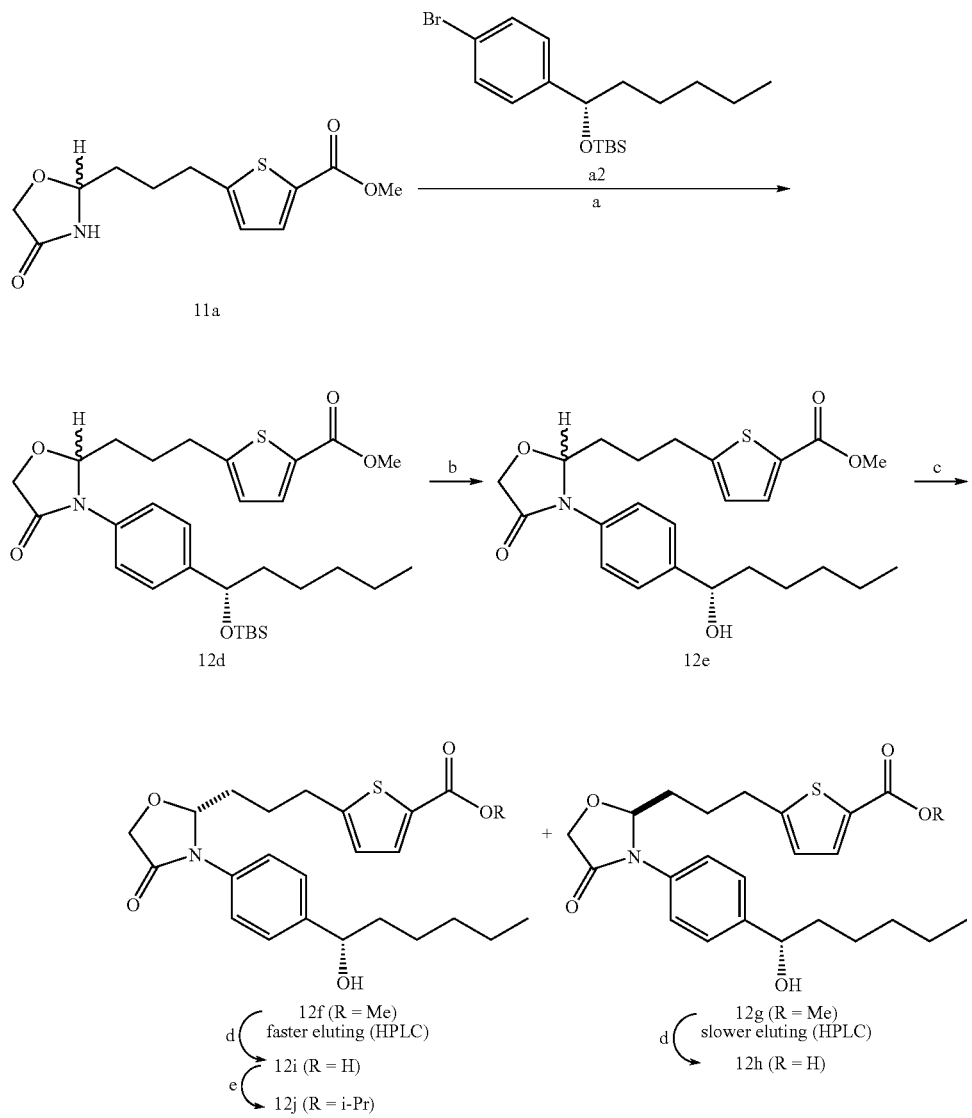

(a) CuI, MeN(H)CH₂CH₂N(H)Me, K₂CO₃, MeCN, reflux; (b) HF-pyridine, MeCN; (c) HPLC separation; (d) Rabbit liver esterase, pH 7.2 buffer, MeCN; (e) i-PrI, DBU, acetone.

EXAMPLE 4

5-(3-((R)-3-(4-((S)-1-hydroxyhexyl)phenyl)-4-oxooxazolidin-2-yl)propyl)thiophene-2-carboxylic acid (12i)

In accordance with the procedure of example 3, step 4, ester 12f (12 mg, 0.027 mmol) was converted into 11 mg (98%) of the title compound (12i) after purification on 4 g silica gel (CH₂Cl₂→20% MeOH/CH₂Cl₂, gradient).

EXAMPLE 5

Isopropyl 5-(3-((R)-3-(4-((S)-1-hydroxyhexyl)phenyl)-4-oxooxazolidin-2-yl)propyl)thiophene-2-carboxylate (12j)

1,8-Diazabicyclo[5.4.0]undec-7-ene (DBU, 5.5 µL, 0.037 mmol) and 2-iodopropane (65 µL, 0.65 mmol) were added to a solution of acid 12i (8 mg, 0.019 mmol) in acetone (0.19 mL) at rt under nitrogen. After 3 d at room temperature, the volatiles were evaporated under a stream of nitrogen. The residue was diluted with water (1 mL), acidified with 1.0 N HCl (1 mL) and extracted with EtOAc (3×10 mL). The combined extracts were washed with brine (5 mL), then dried (Na₂SO₄), filtered and concentrated in vacuo. Purification of the residue by flash column chromatography on 4 g silica (hexanes→EtOAc, gradient) afforded 6.5 mg (74%) of 12j.

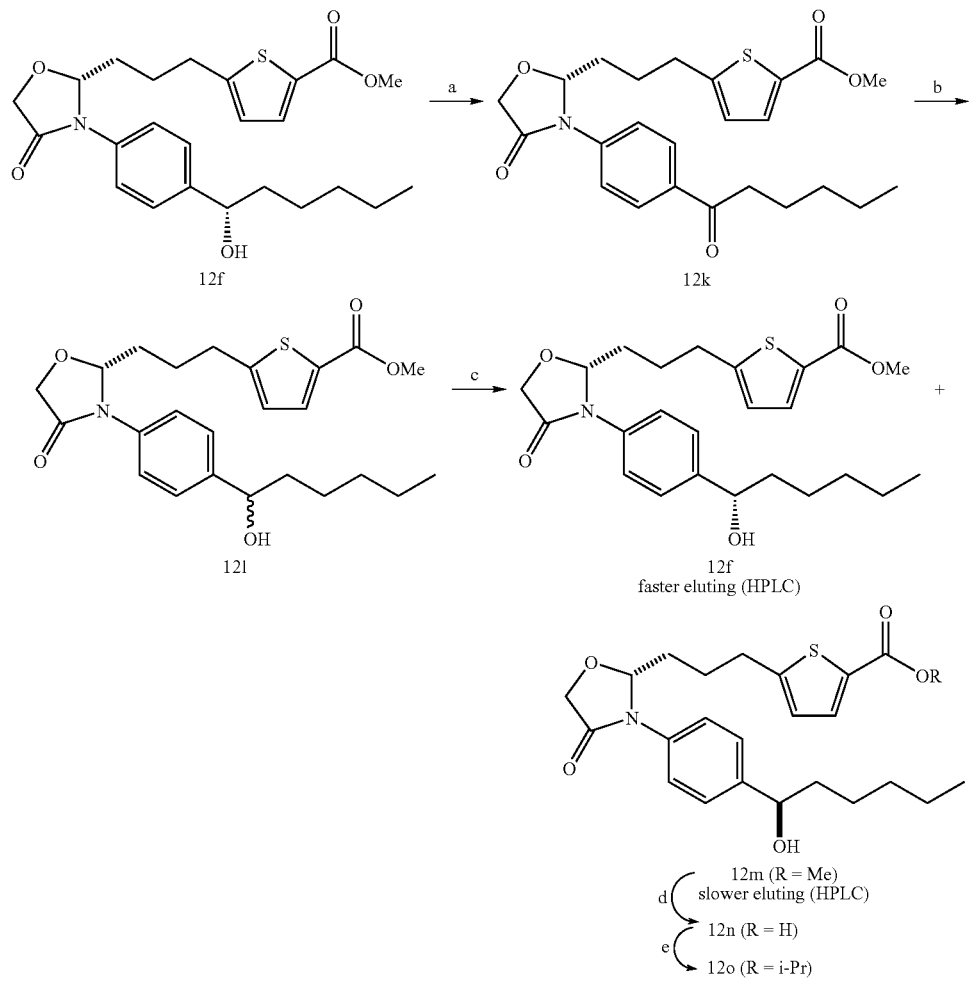

(a) DDQ, CHCl₃, H₂O; (b) NaBH₄, CH₂Cl₂, MeOH; (c) HPLC separation, EtOAc/hexanes;
(d) Rabbit liver esterase, pH 7.2 buffer, MeCN; (e) i-PrI, DBU, acetone.

EXAMPLE 6

5-(3-((R)-3-(4-((R)-1-hydroxyhexyl)phenyl)-4-oxoooxazolidin-2-yl)propyl)thiophene-2-carboxylic acid (12n)

Step 1. Oxidation of 12f to give 12k 2,3-Dichloro-5,6-dicyano-1,4-benzoquinone (DDQ, 43 mg, 0.19 mmol) was added to a mixture of 12f (43 mg, 0.097 mmol) in CHCl₃ (1.0 mL) and water (0.05 mL) at room temperature. The reaction mixture was heated at 40° C. for 18 h. The reaction was cooled to room temperature and was quenched with saturated aqueous NaHCO₃ (10 mL) and extracted with EtOAc (3×20 mL). The combined extracts were washed with saturated aqueous NaHSO₃ (2×25 mL) then dried (Na₂SO₄), filtered and concentrated in vacuo. The crude residue was purified on 12 g silica (hexanes→50% EtOAc/hexanes, gradient) to afford 38 mg (89%) of alcohol 12k.

Step 2. Reduction of 12k to give 12l

Sodium borohydride (5.6 mg, 0.148 mmol) was added in one portion to a solution of 12k (35 mg, 0.079 mmol) in CH₂Cl₂ (0.2 mL) and MeOH (0.2 mL) at 0° C. After 1 h at 0° C., the reaction was allowed to warm to room temperature, was quenched with saturated aqueous NH₄Cl and was extracted with EtOAc (3×15 mL). The combined extracts were dried (Na₂SO₄), filtered and concentrated in vacuo. The crude residue was purified on 4 g silica (hexanes→EtOAc, gradient) to afford 35 mg (99%.) of 12l.

Step 3. HPLC separation of 12l to give 12f and 12m

The two diastereomers of 12l (approximately 34 mg total) were separated on a Waters 600 HPLC instrument employing a Waters 2996 PDA detector and a Phenomenex Luna 10μ prep silica (2) 1 column, 50 mm×250 mm (p/no. 00G-4322-V0; s/no. 356757-1). The flow rate was 45 mL/min, 50% EtOAc/Hex was the eluent and approximately 17 mg of 12l was used in each injection. The first diastereomer (12f) eluted at 67-74 min, and the second diastereomer (12m) eluted at 74-82 min. Two injections afforded 17 mg of 12f and 14 mg of 12m. Retention times varied somewhat over time with the variance in column pressures.

Step 4. Saponification of 12m to give 12n

In accordance with the procedure of example 3, step 4, ester 12m (14 mg, 0.03 mmol) was converted into 13 mg (96%) of the title compound (12n) after purification on 4 g silica gel (CH₂Cl₂→20% MeOH/CH₂Cl₂, gradient).

EXAMPLE 7

Isopropyl 5-(3-((R)-3-(4-((R)-1-hydroxyhexyl)phenyl)-4-oxooxazolidin-2-yl)propyl)thiophene-2-carboxylate (12o)

In accordance with the procedure of example 5, acid 12n (6 mg, 0.014 mmol) was converted into 5 mg (76%) of the title compound (12o).

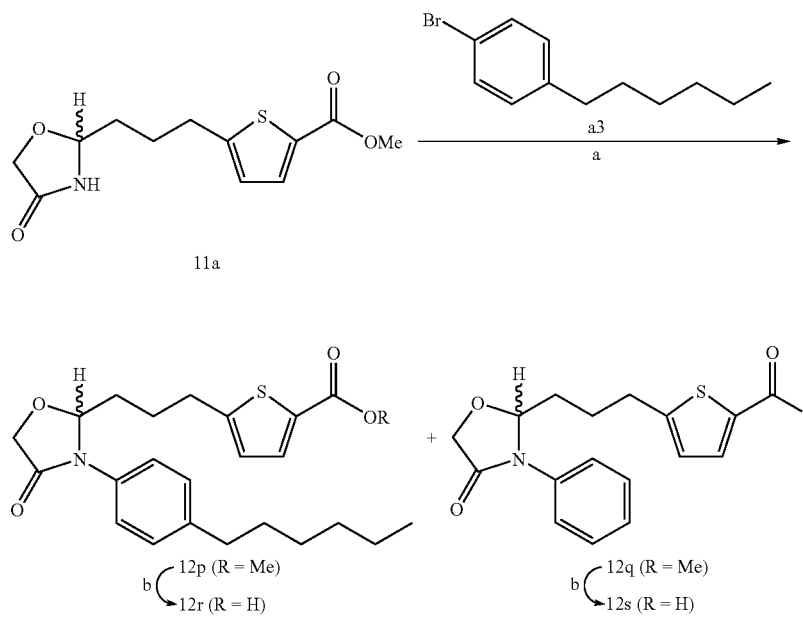

(a) Pd$_2$(dba)$_3$, Xantphos, Cs$_2$CO$_3$, 1,4-dioxane, reflux; (b) Rabbit liver esterase, pH 7.2 buffer, MeCN.

EXAMPLE 8

5-(3-(3-(4-hexylphenyl)-4-oxooxazolidin-2-yl)propyl)thiophene-2-carboxylic acid (12r)

Step 1. Arylation of 11 with a3 to give 12p and 12q

Pd$_2$(dba)$_3$ (30 mg, 0.033 mmol), Xantphos (57 mg, 0.099 mmol) and Cs$_2$CO$_3$ (272 mg, 0.83 mmol) were added sequentially to a solution of 11 (173 mg, 0.64 mmol) and 1-bromo-4-hexylbenzene (a3, commercially available from Alfa Aesar, 165 mg, 0.68 mmol) in 1,4-dioxane (4.5 mL). The flask was fitted with a reflux condenser, evacuated and refilled with nitrogen (5×) then heated at reflux. After 18 h, the reaction was cooled, diluted with EtOAc (25 mL) and filtered through celite, washing with excess EtOAc. The EtOAc filtrate was concentrated in vacuo. The crude residue was purified on 12 g silica gel (hexanes→EtOAc, gradient) to afford 6 mg (2%) of 12p and 7 mg (3%) of 12q along with 88 mg (51%) of starting material 11.

Step 2. Saponification of 12p to give 12r

In accordance with the procedure of example 3, step 4, ester 12p (6 mg, 0.014 mmol) was converted into 2.4 mg (41%) of the title compound (12r) after purification on 4 g silica gel (CH$_2$Cl$_2$→20% MeOH/CH$_2$Cl$_2$, gradient).

EXAMPLE 9

5-(3-(4-oxo-3-phenyloxazolidin-2-yl)propyl)thiophene-2-carboxylic acid (12s)

Rabbit liver esterase (6 mg) was added to a mixture of 12q (7 mg, 0.019 mmol), DMSO (0.2 mL) and pH 7.2 buffer (2.0 mL). The reaction mixture was stirred vigorously for 40 h at rt then was diluted with MeCN (5 mL) and concentrated in vacuo. The crude residue was purified on 4 g silica gel (CH$_2$Cl$_2$→20% MeOH/CH$_2$Cl$_2$, gradient) to afford 3.5 mg (52%) of the title compound (12s).

In Vitro Testing

U.S. Patent Application Publication No. 20070129552, incorporated by reference herein, describes the methods used to obtain the in vitro data in the table below.

| Example | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | hIP | hDP |
| 1 | 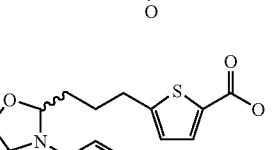 | 4400 | 515 | 17469 | >10000 | 1461 | NA | NA | 8324 | NA | NA | NA |
| 2 | 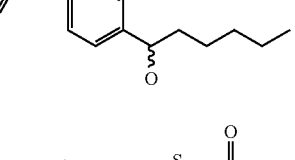 | 8 | 0.06 | 14 | NT | >10000 | NA | NA | 11 | NA | NA | 213 |
| 3 | 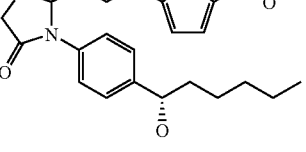 | 82 | 2.9 | 90 | NT | >10000 | NA | NA | 268 | NA | NA | 1972 |
| 4 | 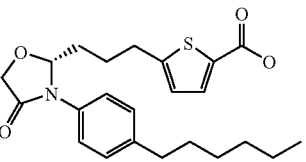 | 1.2 | 0.1 | 7 | NT | >10000 | NA | NA | 4 | NA | NA | 73 |
| 6 | 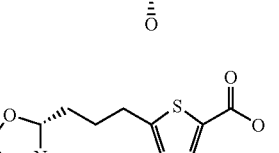 | | | | | | | | | | | |
| 8 | 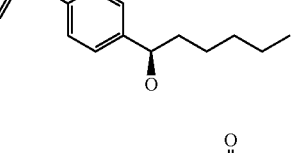 | 37 | 0.24 | 3 | 12646 | 2127 | NA | NA | 237 | NA | NA | 656 |
| 9 | 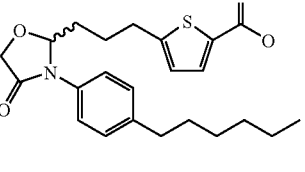 | 3081 | 44 | 680 | >10000 | | NA | NA | NA | NA | NA | >10000 |

In Vivo Testing

U.S. Pat. No. 7,183,324 describes the methods used to obtain the in vitro results presented below.

Isopropyl 5-(3-((R)-3-(4-((S)-1-hydroxyhexyl)phenyl)-4-oxooxazolidin-2-yl)propyl)thiophene-2-carboxylate (12j) was tested in normotensive dogs at 0.003%, dosing once daily for 5 days. The maximum intraocular pressure (IOP) decrease from baseline was 5.4 mmHg (36%) at 54 h; the maximum ocular surface hyperemia (OSH) score was 1.75 at 50 h.

What is claimed is:

1. A compound represented by a formula

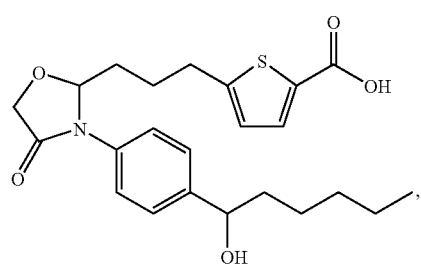

,

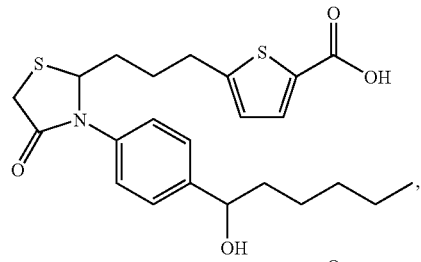

,

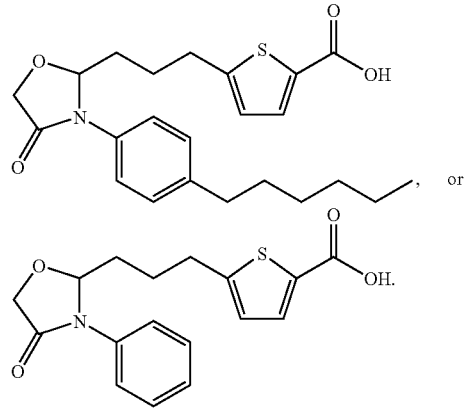

, or

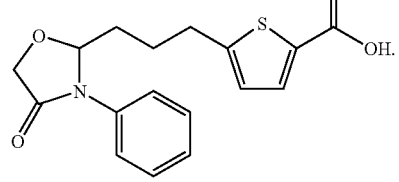

.

2. The compound of claim 1 represented by a structure

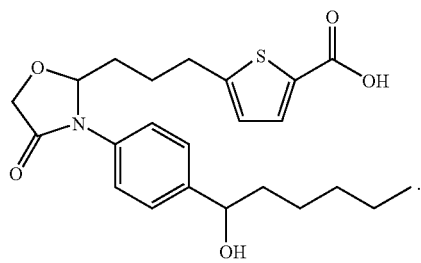

.

3. The compound of claim 1 represented by a structure

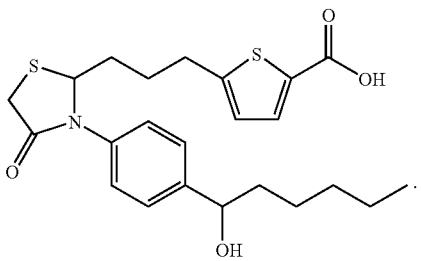

.

4. The compound of claim 1 represented by a structure

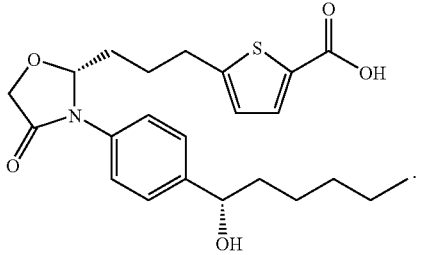

.

5. The compound of claim 1 represented by a structure

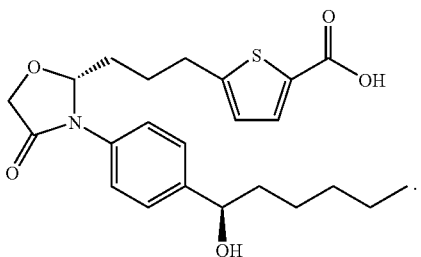

.

6. The compound of claim 1 represented by a structure

7. The compound of claim 1 represented by a structure

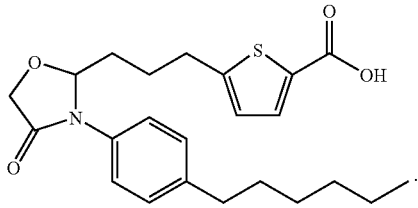

8. The compound of claim 1 represented by a structure

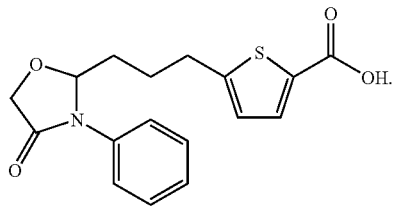

9. A composition comprising a compound of claim 1, wherein said composition is a liquid which is ophthalmically acceptable.

10. A method comprising administering the compound of claim 1 to a mammal for the reduction of intraocular pressure.

11. The method of claim 10 wherein the mammal is a person.

12. The method of claim 10 wherein the compound is represented by a structure

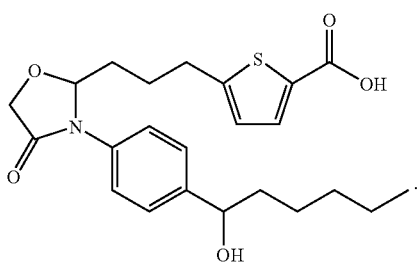

13. The method of claim 10 wherein the compound is represented by a structure

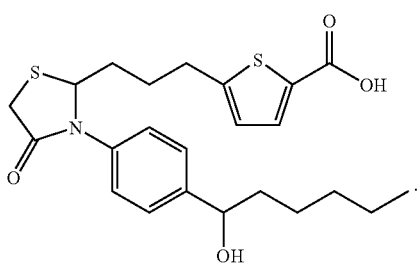

14. The method of claim 10 wherein the compound is represented by a structure

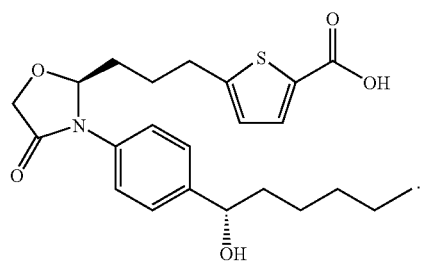

15. The method of claim 10 wherein the compound is represented by a structure

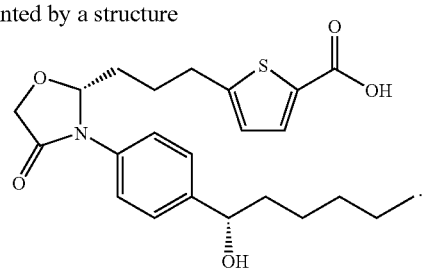

16. The method of claim 10 wherein the compound is represented by a structure

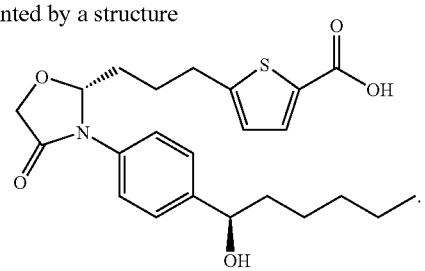

17. The method of claim 10 wherein the compound is represented by a structure

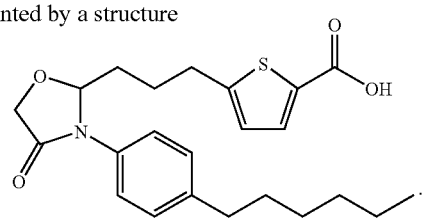

18. The method of claim 10 wherein the compound is represented by a structure

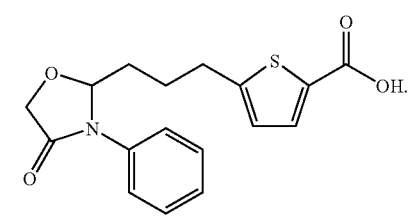

19. A kit comprising a composition comprising the compound of claim 1, a container, and instructions for administration of said composition to a mammal for the treatment of glaucoma or elevated intraocular pressure.

* * * * *

UNITED STATES PATENT AND TRADEMARK OFFICE
CERTIFICATE OF CORRECTION

PATENT NO. : 7,781,465 B2  Page 1 of 1
APPLICATION NO. : 12/192230
DATED : August 24, 2010
INVENTOR(S) : David W. Old It is certified that error appears in the above-identified patent and that said Letters Patent is hereby corrected as shown below:

On the Title page, in Item (56), under "Other Publications", in column 1, line 5, delete "2d" and insert -- $2^{nd}$ --, therefor.

On the Title page, in Item (56), under "Other Publications", in column 1, line 6, delete "Amsterdamn," and insert -- Amsterdam, --, therefor.

In column 3, line 40, after " 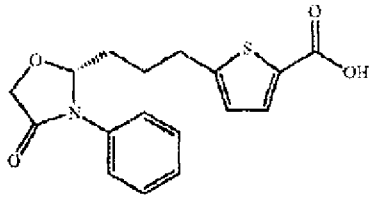 " insert -- . --.

In column 4, line 44, delete "2d" and insert -- $2^{nd}$ --, therefor.

In column 9, line 49, delete "1a" and insert -- 11a --, therefor.

In column 10, line 53, delete "10μ" and insert -- 10 μ --, therefor.

In column 14, line 53, delete "10μ" and insert -- 10 μ --, therefor.

Signed and Sealed this

Nineteenth Day of October, 2010

David J. Kappos
*Director of the United States Patent and Trademark Office*